United States Patent
Ramtirth et al.

(10) Patent No.: US 11,215,470 B2
(45) Date of Patent: Jan. 4, 2022

(54) CONTEXTUAL ROUTE NAVIGATION SYSTEMS

(71) Applicant: Verizon Patent and Licensing Inc., Arlington, VA (US)

(72) Inventors: Ira Ramtirth, Atlanta, GA (US); Ketan Shridhar Adkar, Alpharetta, GA (US); Rickey A. Davis, Jr., Walnut, CA (US); Keith Braddock, Cumming, GA (US); Diego Mondragon, Roswell, GA (US); Charles Forbes Stickels, Milton, GA (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 211 days.

(21) Appl. No.: 16/244,279

(22) Filed: Jan. 10, 2019

(65) Prior Publication Data

US 2020/0225054 A1    Jul. 16, 2020

(51) Int. Cl.
| | | |
|---|---|---|
| *G01C 21/34* | (2006.01) | |
| *B60W 40/08* | (2012.01) | |
| *A61B 5/18* | (2006.01) | |
| *G06K 9/00* | (2006.01) | |

(52) U.S. Cl.
CPC ............ *G01C 21/3484* (2013.01); *A61B 5/18* (2013.01); *B60W 40/08* (2013.01); *G01C 21/3461* (2013.01); *G06K 9/00845* (2013.01); *B60W 2040/0872* (2013.01)

(58) Field of Classification Search
CPC ............ G01C 21/3484; G01C 21/3461; G01C 21/34; B60W 40/08; B60W 2040/0872; B60W 2556/50; B60W 2556/55; G06K 9/00845; A61B 5/01; A61B 5/18; A61B 5/14532; A61B 5/0531; A61B 5/681; A61B 5/225; A61B 5/0022
See application file for complete search history.

(56) References Cited

U.S. PATENT DOCUMENTS

| | | | |
|---|---|---|---|
| 2015/0260531 A1* | 9/2015 | Ehsani | G01C 21/3484 |
| | | | 701/538 |
| 2018/0032691 A1* | 2/2018 | Zur | A61B 5/002 |
| 2018/0094943 A1* | 4/2018 | Grochocki, Jr. ... | G01C 21/3484 |

(Continued)

*Primary Examiner* — James J Lee
*Assistant Examiner* — Shon G Foley

(57) ABSTRACT

A method, system, and computer-readable medium are provided to transmit, via a wireless network from an on-board diagnostic interface coupled to a diagnostic port of a vehicle, telematics data collected during the vehicle's operation; transmit, via the wireless network from a monitoring device, physiological data obtained for the vehicle's operator at corresponding points in time during the vehicle's operation; determine multiple roadway locations of the vehicle at the corresponding points in time, using the telematics data; determine a physiological state of the operator at each of the multiple roadway locations at the corresponding points in time, using the physiological data; determine, using the physiological states, a stress level profile associated with the operator for each travel route to a destination and including the multiple roadway locations, and send, to the operator, a recommendation identifying travel routes based on the associated stress level profiles.

20 Claims, 10 Drawing Sheets

(56) References Cited

U.S. PATENT DOCUMENTS

2019/0316922 A1* 10/2019 Petersen ............ G01C 21/3617
2019/0332902 A1* 10/2019 Gallagher .......... G06K 9/00335
2019/0367039 A1* 12/2019 Persia ................ G06Q 30/0201
2020/0219615 A1*  7/2020 Rabin .................... G16H 20/70

* cited by examiner

CONTEXTUAL ROUTE NAVIGATION SYSTEMS

BACKGROUND INFORMATION

Generally, route navigation systems present users with recommended travel routes which are calculated based on travel time, distance, and/or mode of travel (e.g., motor vehicle, walking, etc.). Some navigation systems further give users the option to include/filter out certain routes based on roadway characteristics (e.g., highway or non-highway, toll or toll-free), for example.

DETAILED DESCRIPTION OF PREFERRED EMBODIMENTS

Figure 1:
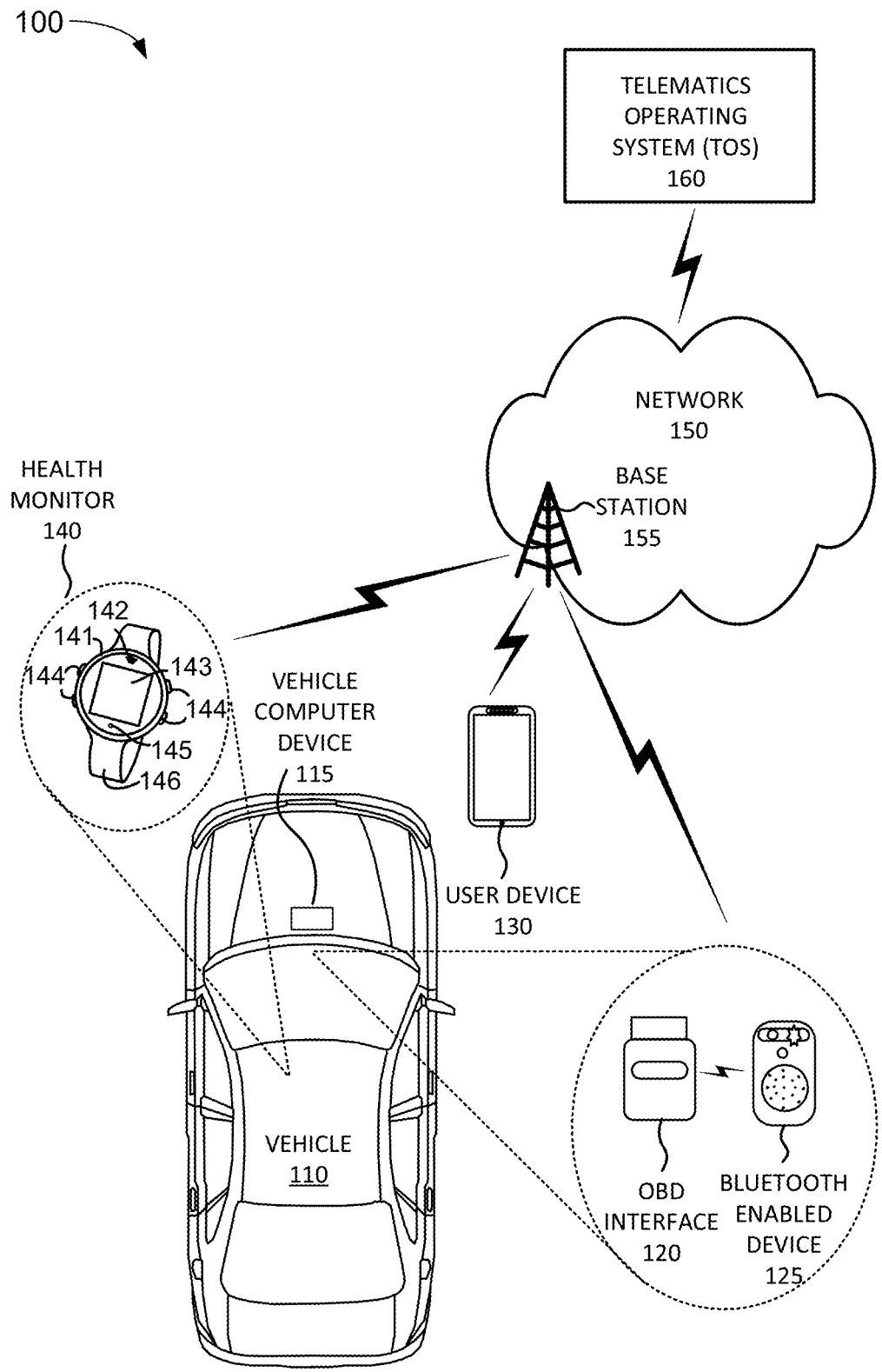
FIG. 1 is a diagram illustrating an environment according to an implementation described herein.

The following detailed description refers to the accompanying drawings. The same reference numbers in different drawings identify the same or similar elements.

Individuals' driving experiences can vary by route due to, for example, engineered roadway features and/or other types of conditions pertaining to the route. Some driving conditions/combinations of conditions tend to involuntarily induce stress among some drivers. Stressed drivers may exhibit physiological characteristics indicative of their stress levels. Current navigation systems do not automatically customize route recommendations for a particular user in response to a navigation query from that user. For instance, state of the art navigation technology does not use machine learning to account for varied driver experiences and corresponding stress-inducing levels associated with different roads and/or different stretches of a road. Presently, route recommendation systems do not aggregate drivers' experiences to assign relative stress profiles, for example, for use in determining alternative route segments.

Roadway engineering that impacts driver stress to varying degrees depending on the driver may include one-way, two-way, or divided two-way driving, applicable speed limits, changes in speed limits, school zones, construction zones, traffic control systems (e.g., stop lights), pedestrian cross-walks, type of lighting (e.g., artificial, natural, etc.), roadside parking, lane width, pavement markings, signage, number of driving lanes, turning lanes, cross streets, persistent traffic patterns, frequency of traffic incidents, road surface conditions, tunnels, bridges, proximity to bodies of water, guardrails, grade, shoulder width, sun glare, elevated roadways, ingress/egress (e.g., driveways), curviness of the road, roadside distractions (e.g., pedestrians, lighting, etc.), visibility, etc. In addition, overall travel conditions that impact driver stress include the number of turns involved, noise, the number of streets traveled, merging traffic, braking, accelerating, familiarity with the area, weather conditions, time-of-day, day-of-week, season, etc. Physiological indicators of driver stress may include detectable changes in heart rate, blood glucose levels, blood pressure, body temperature, perspiration, respiratory rate, hormone (e.g., adrenaline, cortisol, etc.) production, eye movement, muscle tension (e.g., hand grip), verbalizing (e.g., yelling, muttering, cursing, etc.), honking, and/or other types of observable reactions by the driver.

A vehicle's on-board diagnostics (OBD) system may be equipped with a serial connection interface, such as an OBD or an OBD-II port, which is configured to connect an engine control module (ECM) to a diagnostics reader that collects vehicle information (e.g., performance and/or tracking data). The diagnostics or OBD-II reader may include a transceiver configured to communicate via a wireless network to a server per a vehicle telematics service that may be accessible to a subscriber via an application on a mobile device (e.g., cell phone). The OBD-II reader may also be configured to wirelessly connect to a speaker device or console device in the vehicle to functionally provide "travel companion services" to a driver and/or vehicle occupant (e.g., a passenger, etc.).

Implementations described herein provide technological solutions to navigation challenges by integrating outputs from a motor vehicle's OBD system and a driver's health monitoring system(s) to present contextual navigation results responsive to the driver's navigation query. In some implementations, a customized navigation route(s) generated at a server of a telematics service provider is transmitted via a wireless network to a subscriber executing a telematics application. The server automatically identifies the customized travel route(s) for the subscriber based on designated stress-levels of the prospective routes. The prospective routes may minimize the driving stress that the subscriber is subjected to relative to other potential routes. The server may transmit the recommended route(s) via the wireless network to the OBD-II reader on board a vehicle and/or a user device associated with the subscriber.

FIG. 1 is a diagram illustrating exemplary components of an environment 100 according to an implementation described herein. As shown in FIG. 1, environment 100 may include a vehicle 110, an on-board diagnostics (OBD) interface 120, a Bluetooth®-enabled device 125, a user device 130, a health monitor 140, a network 150, and a telematics operating system (TOS) 160.

Vehicle 110 may include a car, a sports utility vehicle (SUV), a truck, a van, and/or another type of motor vehicle. Vehicle 110 may be a passenger vehicle and/or another vehicle used for transportation by an operator. Vehicle 110 includes a cabin space that seats the operator and possibly one or more passengers ("occupants"). The operator of vehicle 110 may be a subscriber to a telematics subscription service, such as HUM® by Verizon®. Furthermore, vehicle 110 may include a vehicle computer device 115.

Vehicle computer device 115 may manage one or more functions of vehicle 110 and/or may collect information relating to vehicle 110. For example, vehicle computer device 115 may include an ECM, an engine control unit (ECU) or another powertrain control module (PCM). Vehicle computer device 115 may manage the functionality of various components of vehicle 110; collect data about the status of the components of vehicle 110; report error and/or trouble codes received from components of vehicle 110; generate maintenance schedule notifications for vehicle 110; and/or collect telematics information relating to vehicle 110 such as the location of vehicle 110 (i.e., tracking data), performance monitoring of vehicle 110, emergency incident detection, etc., for example, in real-time. Vehicle computer device 115 may obtain sensor information from one or more sensors located in vehicle 110, such as an accelerometer, a voltage meter, a dashboard camera, and/or other types of monitoring devices, such as health monitor 140 that collects physiological data of the operator of vehicle 110, as described below.

OBD interface 120 may include a device, such as a dongle device, that may connect to (e.g., be plugged into) an OBD port in vehicle 110, such as an OBD-II port or another type of OBD port. The OBD port may be located, for example, inside vehicle 110, such as on the dashboard, under the steering wheel, or in another location. OBD interface 120 may interface with vehicle computer device 115 and/or with other vehicle components of vehicle 110, may obtain diagnostics and/or telematics information about vehicle 110, and may report the obtained information to TOS 160. OBD interface 120 may interface with sensors, such as integrated physiological sensors.

Furthermore, OBD interface 120 may include electronics (e.g., a transceiver) for wired and/or wireless network connectivity (e.g., short-range and/or long-range) that enables OBD interface 120 to collect, store, and exchange data. Long-range network connectivity may include, for example, Wi-Fi and/or cellular network connectivity, and enable communication with TOS 160 via network 150 and/or another network device. Short-range network connectivity may include, for example, Bluetooth® and/or Bluetooth® Low Energy (BLE) connectivity, and enable communication with Bluetooth®-enabled device 125, user device 130, and/or health monitor 140.

Bluetooth®-enabled device 125 may include an audio device that wirelessly connects to OBD interface 120 using a short range wireless communication protocol (e.g., Bluetooth®, WiFi, etc.). Bluetooth®-enabled device 125 may be capable of receiving information, such as audio files, from OBD interface 120, and outputting audio for an occupant of vehicle 110, when Bluetooth®-enabled device 125 is located in vehicle 110 (e.g., mounted to a visor and/or a console, etc.). Bluetooth®-enabled device 125 may be battery operated and configured to send and/or receive data via a lower power transceiver. In other implementations, Bluetooth®-enabled device 125 may be part of vehicle 110's radio/speaker system.

In some implementations, Bluetooth®-enabled device 125 may include one or more visual indicators (e.g., light-emitting diode (LED) display, liquid-crystal display (LCD), icons, etc.) to display information received from OBD interface 120, for example, that is related to the audio information, to an operator and/or occupant of vehicle 110. Bluetooth®-enabled device 125 may include one or more input devices (e.g., button, switch, keypad, motion sensor, etc.) for use by an occupant of vehicle 110 for controlling one or more functions (e.g., power, volume, signaling, etc.) of Bluetooth®-enabled device 125. In some implementations, a microphone may be associated with Bluetooth®-enabled device 125, which is capable of receiving/recording audio.

User device 130 may be associated with the driver of vehicle 110 and/or the subscriber of a telematics subscription service. User device 130 may include a mobile communication device such as a mobile phone, a smart phone, a tablet computer, a laptop computer, a phablet computer device, a wearable computer device (e.g., a glasses smartphone device, a wristwatch smartphone device, etc.), and/or any other type of mobile computer device with wireless communication and output capabilities. User device 130 may communicate with TOS 160 via network 150 using a wireless access point (e.g., base station 145), for example, by executing an application, resident on user device 130, relating to a telematics subscription service. In one embodiment, user device 130 may communicate with OBD interface 120 and/or health monitor 140 using a short-range wireless communication protocol (e.g., Bluetooth®, WiFi, etc.). In some embodiments, user device 130 may execute a settings component for the health monitoring application and the telematics tracking application operating on health monitor 140 and OBD interface 120, respectively.

Health monitor 140 may include any device that obtains and/or measures physiological data of a driver substantially in real-time, and include any wearable device such as personal fitness technology (e.g., Fitbit®, Misfit®, etc.), glucose meters, special-purpose watches (e.g., Apple Watch®) and/or glasses (e.g., Google Glass®), etc. Additionally or alternatively, health monitor 140 may be integrated into vehicle equipment, such as the console, visor, seat, and/or steering wheel, which may incorporate pulse rate monitors, thermometers, conductivity meters (e.g., for correlating to perspiration levels), and/or dynamometric devices (e.g., to measure hand grip tension). Once obtained from one or more of these sources, the physiological data may be stored and/or transmitted via wireless network 150 to, for example, TOS 160 for processing.

For example, health monitor 140 may include a dynamometric device in the steering wheel which indicates the amount of pressure with which the operator is gripping the steering wheel. In one embodiment, health monitor 140 may include a pulse rate monitor in the steering wheel that obtains pulse rate data of the operator. In another embodiment, health monitor 140 may include a thermometer that obtains the operator's body temperature, located in the steering wheel or the driver seat, for example. In some embodiments, health monitor 140 may include a camera device located at a visor to capture images of the operator's face that may be used to determine eye movement and/or other types of observable behavior. Health monitor 110 may include other sensors capable of obtaining other types of physiological data of the operator.

In an embodiment, health monitor 140 may include a wearable device that includes a housing 141, a speaker 142, a display 143, control buttons 144, a microphone 145, and/or a strap/band 146. Housing 141 may contain the functional components of health monitor 140 and attach to strap 146. Speaker 142 may provide audible information to the operator of vehicle 110. For example, speaker 142 may provide ringtones, beeping sounds or other sounds to alert the operator to a triggering event. For example, speaker 142 may be configured to output an alert relating to a triggering event identified by TOS 160, such as operation of vehicle 110 in a potential fatigue zone and/or a detected fatigue state of the operator. Speaker 142 may also output audio information or instructions to a user of user device 105.

Display 143 may provide visual information to the operator. For example, display 143 may include a liquid crystal display (LCD), a touch screen display or another type of display used to provide information to the user, such as text and/or graphics regarding GPS location information, health or wellness status information (e.g., pulse rate, blood pressure, blood sugar level, etc.), incoming or outgoing voice communications, and/or incoming or outgoing electronic mail (email), instant messages (e.g., mobile instant messages (MIMs), short message service (SMS) messages, multimedia message service (MMS) messages, etc. Display 143 may also display information regarding various applications, such as a subscription telematics application and/or a route navigation application, etc.

Control buttons 144 may permit the operator to interact with user device 130 to cause user device 130 to perform one or more operations, such as send communications (e.g., text messages or multi-media messages), launch an application program, such as a trip monitoring/tracking program. Further, one of control buttons 144 may be a menu button that permits the user to view options associated with executing various application programs, such as the trip monitoring/tracking program, interacting with user device 130. In some implementations, functions associated with control buttons 144 may be duplicated or replaced by other interactive control elements, such as a touch screen display 143 or an interactive voice response (IVR) system. Microphone 145 may receive audible information from the operator, such as telephone communications and/or voice input. Strap 146 may include any mechanism for removably securing health monitor 140 to the operator or the operator's clothing.

As illustrated, health monitor 140 may be provided in one of a variety of user-wearable form factors, such as the style depicted in FIG. 1, designed to be worn on the wrist of a user. Although not illustrated, other exemplary wearable form factors for health monitor 140 may include a pendant style device configured for wearing via a chain or lanyard, a brooch or other pin-on or clip-on style device, a ring, etc. Furthermore, the elements of health monitor 140 may be incorporated into other user devices, such as a wireless headset, glasses, etc. Such wearable form factors may facilitate increased reliability and ease of use of health monitoring device 140.

Network 150 may include one or more circuit-switched networks and/or packet-switched networks. For example, network 150 may include a local area network (LAN), a wide area network (WAN), a metropolitan area network (MAN), a Public Switched Telephone Network (PSTN), an ad hoc network, an intranet, the Internet, a fiber optic-based network, a wireless network, a satellite network, and/or a combination of these or other types of networks. Network 150 may include base station 155.

Base station 155 may function as an access point that enables vehicle computer device 115, OBD interface 120, user device 130, and/or health monitor 140 to wirelessly connect to network 150. For example, base station 155 may include a Long Term Evolution (LTE) eNodeB base station, a Global System for Mobile Communications (GSM) base station, a Code Division Multiple Access (CDMA) base station, and/or another type of base station.

TOS 160 may include one or more devices, such as computer devices and/or server devices, which may be configured to receive telematics information from OBD interface 120 and/or from vehicle computer device 115, communications from user device 130, and physiological data from health monitor 140. Furthermore, in some implementations, TOS 160 may perform some or all of the processing for correlating geographic locations and physiological data received from subscribers' OBD interfaces 120 and health monitors 140, respectively. In some implementations, TOS 160 may assign stress level profile values for identifiable roadway segments using the geographic locations/physiological data correlations. TOS 160 may further determine contextual route recommendations based on the stress level profiles for roadway segments connecting a point of origin and a destination identified in a navigation query. TOS 160 may interface with other systems (not shown in FIG. 1), such as a database that logs geographic location information and corresponding physiological data reported for subscribers.

Although FIG. 1 shows exemplary components of environment 100, in other implementations, environment 100 may include fewer components, different components, differently arranged components, or additional components than depicted in FIG. 1. Additionally or alternatively, one or more components of environment 100 may perform functions described as being performed by one or more other components of environment 100.

Figure 2:
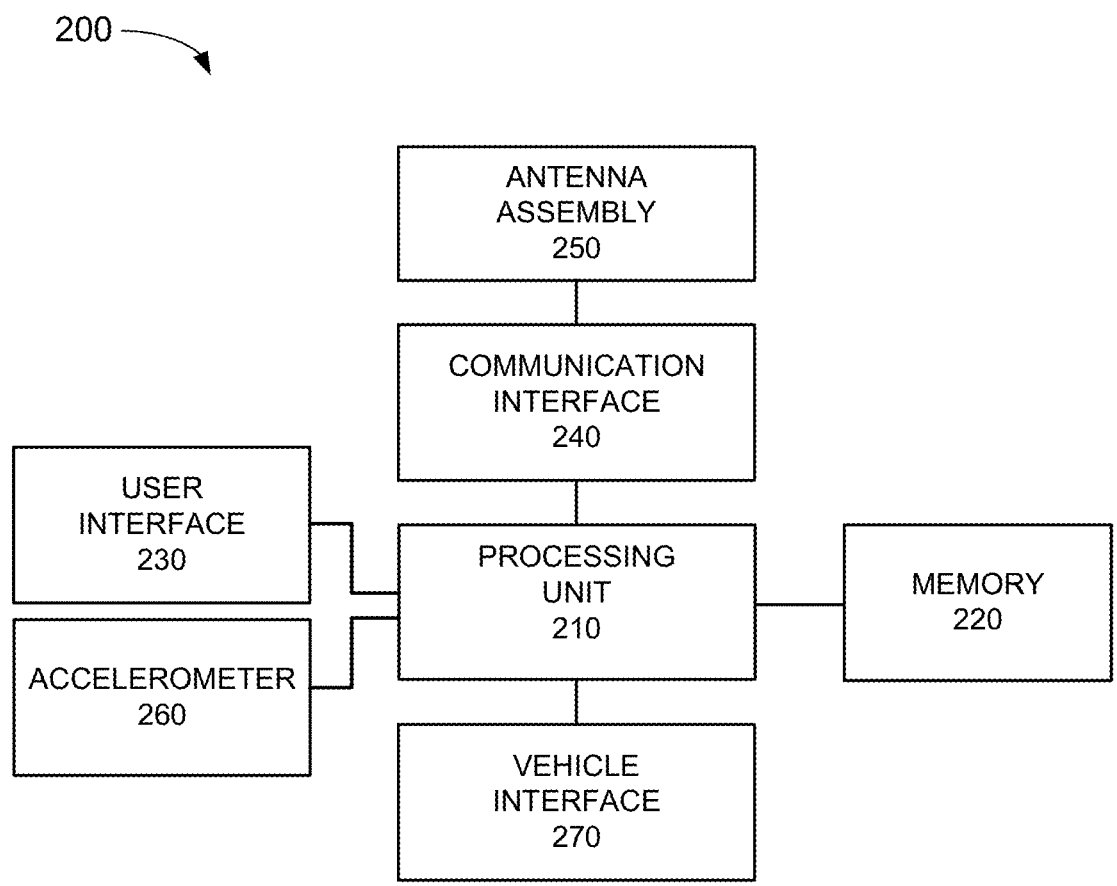
FIGS. 2 and 3 are diagrams illustrating exemplary components of one or more of the devices of FIG. 1.

FIG. 2 is a diagram illustrating exemplary components of device 200 according to an implementation described herein. Vehicle computer device 115, OBD interface 120, speaker device 125, user device 130, and/or health monitor 140 may each include one or more devices 200. As shown in FIG. 2, device 200 may include a processing unit 210, a memory 220, a user interface 230, a communication interface 240, and an antenna assembly 250. If device 200 is included in OBD interface 120, device 200 may further include an accelerometer 260, and a vehicle interface 270.

Processing unit 210 may include one or more processors, microprocessors, application specific integrated circuits (ASICs), field programmable gate arrays (FPGAs), and/or other processing logic. Processing unit 210 may control operation of device 200 and one or more of its components.

Memory 220 may include a random access memory (RAM) or another type of dynamic storage device, a read only memory (ROM) or another type of static storage device, a removable memory card, and/or another type of memory to store data and instructions that may be used by processing unit 210.

User interface 230 may allow a user to input information to device 200 and/or to output information from device 200. Examples of user interface 230 may include a speaker to receive electrical signals and output audio signals; a camera to receive image and/or video signals and output electrical signals; a microphone to receive sounds and output electrical signals; buttons (e.g., a joystick, control buttons, a keyboard, or keys of a keypad) and/or a touchscreen to receive control commands; a display, such as an LCD, to output visual information; an actuator to cause device 200 to vibrate; a sensor; and/or any other type of input or output device.

Communication interface 240 may include a transceiver that enables device 200 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 240 may include a transmitter that converts baseband signals to radio frequency (RF) signals and/or a receiver that converts RF signals to baseband signals. Communication interface 240 may be coupled to antenna assembly 250 for transmitting and receiving RF signals.

Communication interface 240 may include a logical component that includes input and/or output ports, input and/or output systems, and/or other input and output components that facilitate the transmission of data to other devices. For example, communication interface 240 may include a network interface card (e.g., Ethernet card) for wired communications and/or a wireless network interface (e.g., a WiFi)

card for wireless communications. Communication interface 240 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

Antenna assembly 250 may include one or more antennas to transmit and/or receive RF signals. Antenna assembly 250 may, for example, receive RF signals from communication interface 240 and transmit the signals via an antenna and receive RF signals from an antenna and provide them to communication interface 240.

As described herein, device 200 may perform certain operations in response to processing unit 210 executing software instructions contained in a computer-readable medium, such as memory 220. A computer-readable medium may be defined as a non-transitory memory device. A non-transitory memory device may include memory space within a single physical memory device or spread across multiple physical memory devices. The software instructions may be read into memory 220 from another computer-readable medium or from another device via communication interface 240. The software instructions contained in memory 220 may cause processing unit 210 to perform processes that will be described later. Alternatively, hard-wired circuitry may be used in place of, or in combination with, software instructions to implement processes described herein. Thus, implementations described herein are not limited to any specific combination of hardware circuitry and software.

Accelerometer 260 may be configured to measure acceleration of device 200. Accelerometer 260 may include a piezoelectric, piezoresistive, capacitive, micro electro-mechanical system (MEMS), and/or another type of accelerometer 260. Accelerometer 260 may record vibrations of device 200 in response to operation and/or movement of vehicle 110. Vehicle interface 270 may include one or more ports and associated logic to communicate with vehicle computer device 115 and/or other electronic components of vehicle 110. For example, vehicle interface 270 may include an OBD I port, an OBD II port, and/or another type of vehicle interface.

Although FIG. 2 shows exemplary components of device 200, in other implementations, device 200 may include fewer components, different components, differently arranged components, or additional components than those depicted in FIG. 2. Additionally or alternatively, one or more components of device 200 may perform the tasks described as being performed by one or more other components of device 200.

Figure 3:
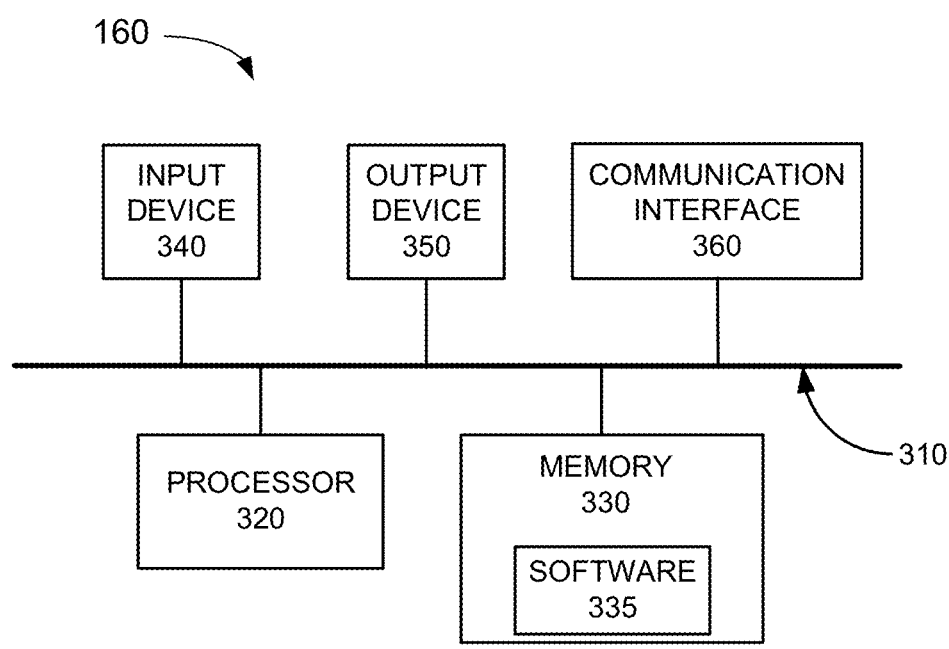

FIG. 3 is a diagram illustrating exemplary components of TOS 160 according to an implementation described herein. As shown in FIG. 3, TOS 160 may include a bus 310 that provides a path that permits communication among a processor 320, a memory 330 that stores software 335, an input device 340, an output device 350, and a communication interface 360.

Processor 320 may include any type of single-core processor, multi-core processor, microprocessor, latch-based processor, and/or processing logic (or families of processors, microprocessors, and/or processing logics) that interprets and executes instructions. In other embodiments, processor 320 may include an application-specific integrated circuit (ASIC), a field-programmable gate array (FPGA), and/or another type of integrated circuit or processing logic.

Memory 330 may include any type of dynamic storage device that may store information and/or instructions, for execution by processor 320, and/or any type of non-volatile storage device that may store information for use by processor 320. For example, memory 330 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Software 335 includes an application or a program that provides a function and/or a process. As an example, with reference to TOS 160, software 335 may include an application that, when executed by processor 320, provides the functions of driver health monitoring/location tracking, as described herein. Also, software 335 may include an application that, when executed by processor 320, provides the functions related to assessing routes for driver stress, as described herein. Further, TOS 160 may use the assessed stress profiles to perform route recommendation that is individualized to the requestor. Software 335 may also include firmware, middleware, microcode, hardware description language (HDL), and/or other form of instruction. Software 335 may further include an operating system.

Input device 340 may allow an operator to input information into TOS 160. Input device 340 may include, for example, a keyboard, a mouse, a pen, a microphone, a remote control, an audio capture device, an image and/or video capture device, a touch-screen display, and/or another type of input device. In some embodiments, TOS 160 may be managed remotely and may not include input device 340. In other words, TOS 160 may be "headless" and may not include a keyboard, for example.

Output device 350 may output information to an operator of TOS 160. Output device 350 may include a display, a printer, a speaker, and/or another type of output device. For example, TOS 160 may include a display, which may include a liquid-crystal display (LCD) for displaying content to a user. In some embodiments, TOS 160 may be managed remotely and may not include output device 350. In other words, TOS 160 may be "headless" and may not include a display, for example.

Communication interface 360 may include a transceiver that enables TOS 160 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 360 may include a transmitter that converts baseband signals to radio frequency (RF) signals and/or a receiver that converts RF signals to baseband signals. Communication interface 360 may be coupled to an antenna for transmitting and receiving RF signals.

Communication interface 360 may include a logical component that includes input and/or output ports, input and/or output systems, and/or other input and output components that facilitate the transmission of data to other devices. For example, communication interface 360 may include a network interface card (e.g., Ethernet card) for wired communications and/or a wireless network interface (e.g., a WiFi) card for wireless communications. Communication interface 360 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, TOS 160 may perform certain operations relating to contextual route recommendation. TOS 160 may perform these operations in response to processor 320 executing software 335 instructions contained in a computer-readable medium, such as memory 330. A computer-readable medium may be defined as a non-transitory memory device. A memory device may be implemented within a single physical memory device or spread across multiple physical memory devices. Software 335 instructions may be read into memory 330 from another computer-readable medium or from another device. Software instructions 335 contained in memory 330 may cause processor 320 to perform processes described herein. Alternatively, hardwired circuitry may be used in place of, or in combination with, software instructions to implement processes described herein. Thus, implementations described herein are not limited to any specific combination of hardware circuitry and software.

Although FIG. 3 shows exemplary components of TOS 160, in other implementations, TOS 160 may include fewer components, different components, additional components, or differently arranged components than those depicted in FIG. 3. Additionally or alternatively, one or more components of TOS 160 may perform one or more tasks described as being performed by one or more other components of TOS 160.

Figure 4:
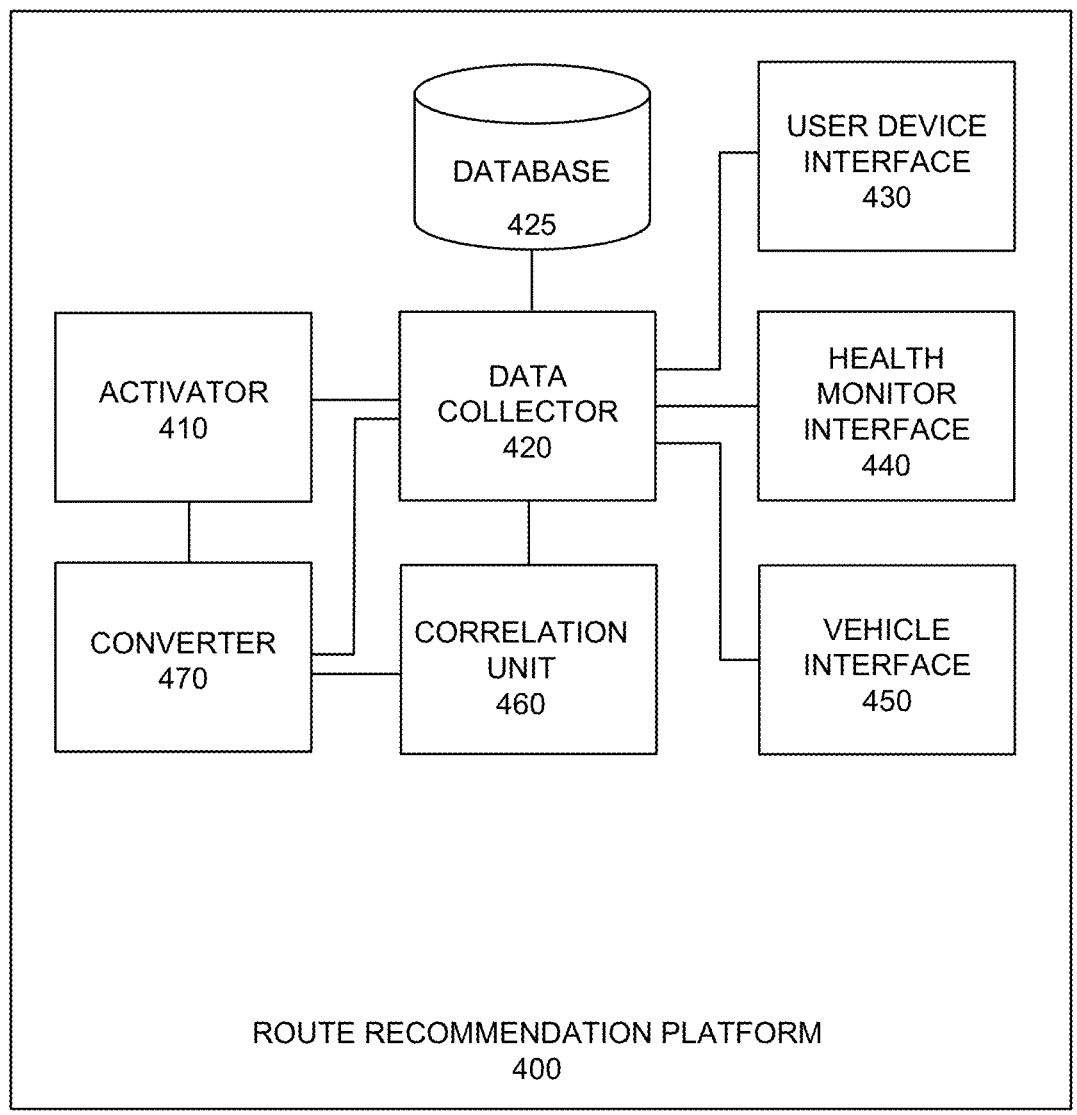
FIG. 4 is a diagram illustrating exemplary functional components of a route recommendation platform that may be implemented in one or more of the devices of FIG. 1.

FIG. 4 is a diagram illustrating exemplary functional components of a route recommendation engine 400 according to a first implementation described herein. Route recommendation engine 400 may be implemented, for example, via processing unit 210 of device 200 (e.g., OBD interface 120, vehicle computer device 115, user device 130, health monitor 140, etc.) executing instructions from memory 220. Alternatively, some or all of the functionality of route recommendation engine 400 may be implemented via hardwired circuitry. In other implementations, some or all of the functional components of route recommendation engine 400 may be implemented via processor 320 executing software 335 instructions from memory 330 of TOS 160.

As shown in FIG. 4, a route recommendation platform 400 may include an activator 410, a data collector 420, a database (DB) 425, a user device interface 430, a telematics system interface 440, a vehicle interface 450, a correlation unit 460, and/or a converter 470.

Figure 5A:
FIGS. 5A-5E are diagrams illustrating exemplary user interfaces of a wearable device according to an implementation described herein.
Figure 5B:
Figure 5C:

Activator 410 may activate route recommendation platform 400 in response to detecting a trip-on event. The trip-on event may include the operator of vehicle 110 entering identifying information (e.g., username, email address, etc., for a registered user) into a trip monitoring/tracking application residing on user device 130, in response to a prompt 510 displayed via display 143, as illustrated in FIG. 5A, for example. In some embodiments, other detected events may activate route recommendation platform 400. For example, acceleration of vehicle 110, or any other detected operation (e.g., ignition, etc.) of vehicle 110 may automatically trigger trip recording functions. Once activated, display 143 may present "On/Off" icons 520, as shown in FIG. 5B for example. Activator 410 may instruct data collector 420 to collect data associated with the trip in response to operator input selecting "On" 530, as shown in FIG. 5C, for example.

Figure 5D:
Figure 5E:

Data collector 420 may collect data from multiple data sources and store the data in database (DB) 425. In some implementations, data collector 420 may collect the data at regular and/or irregular intervals (e.g., every few seconds). Data collector 420 may collect location data from vehicle computer device 115 and/or physiological data from health monitor 140, from one or more vehicle sensors, and/or from other sources of data. Data collector 420 may cease collecting the data at any point during the trip and/or at completion of the trip, in response to user input selecting "Off" 540 via display 143, as shown in FIG. 5D for example. Display 143 may display an indication 550 to the operator that data was recorded for the trip, or the like, as shown in FIG. 5E for example.

User device interface 430 may be configured to communicate with user device 130. As an example, user device interface 430 may receive wireless communications from user device 130. Health monitor interface 440 may be configured to communicate with health monitor 140. Vehicle interface 450 may be configured to communicate with OBD 120 and/or with Bluetooth®-enabled device 125.

Correlation unit 460 may be configured to map trip location data to trip physiological data that is obtained for a traveled route and/or a route segment. For example, in some implementations, correlation device 460 may use data retrieved from DB 425 and/or other information to identify, for the operator, biometric information corresponding to physical locations (e.g., using latitude and longitude coordinate information). When multiple types of physiological data (e.g., heart rate and blood sugar level) are obtained for the operator, correlation device 460 may correlate each reading to a given location separately or, in some implementations, create a physiological index that reflects values for each data type. In some embodiments, the physiological index may be normalized (e.g., between 0 and 1.0). When multiple readings of the same data type are recorded for a given location (e.g., multiple trips recorded for the operator, trips recorded for multiple operators (e.g., 10's, 100's, 1,000's, etc.)), correlation device 460 may, for example, average the physiological data values for that location. In one embodiment, physiological data for different operators may be aggregated for each route segment that is monitored.

Converter 470 may be configured to convert physiological data values into health-related classifications for routes and/or route segments. Based on the health-related classifications, converter 470 may calculate, for example, stress-related profiles for routes, using the health-related classifications for the constituent route segments. In one embodiment, converter 470 may rank order proposed routes according to the relative stress-related profiles. In one implementation, converter 470 may convert the health-related classifications into other profiles, such as fatigue-related profiles, that may be used to identify potential driver fatigue zones along a given route.

Although FIG. 4 shows exemplary functional components of route recommendation platform 400, in other implementations, route recommendation platform 400 may include fewer functional components, different functional components, differently arranged functional components, or additional functional components than depicted in FIG. 4. Additionally, or alternatively, one or more functional components of route recommendation platform 400 may perform functions described as being performed by one or more other functional components of route recommendation platform 400.

Figure 6:
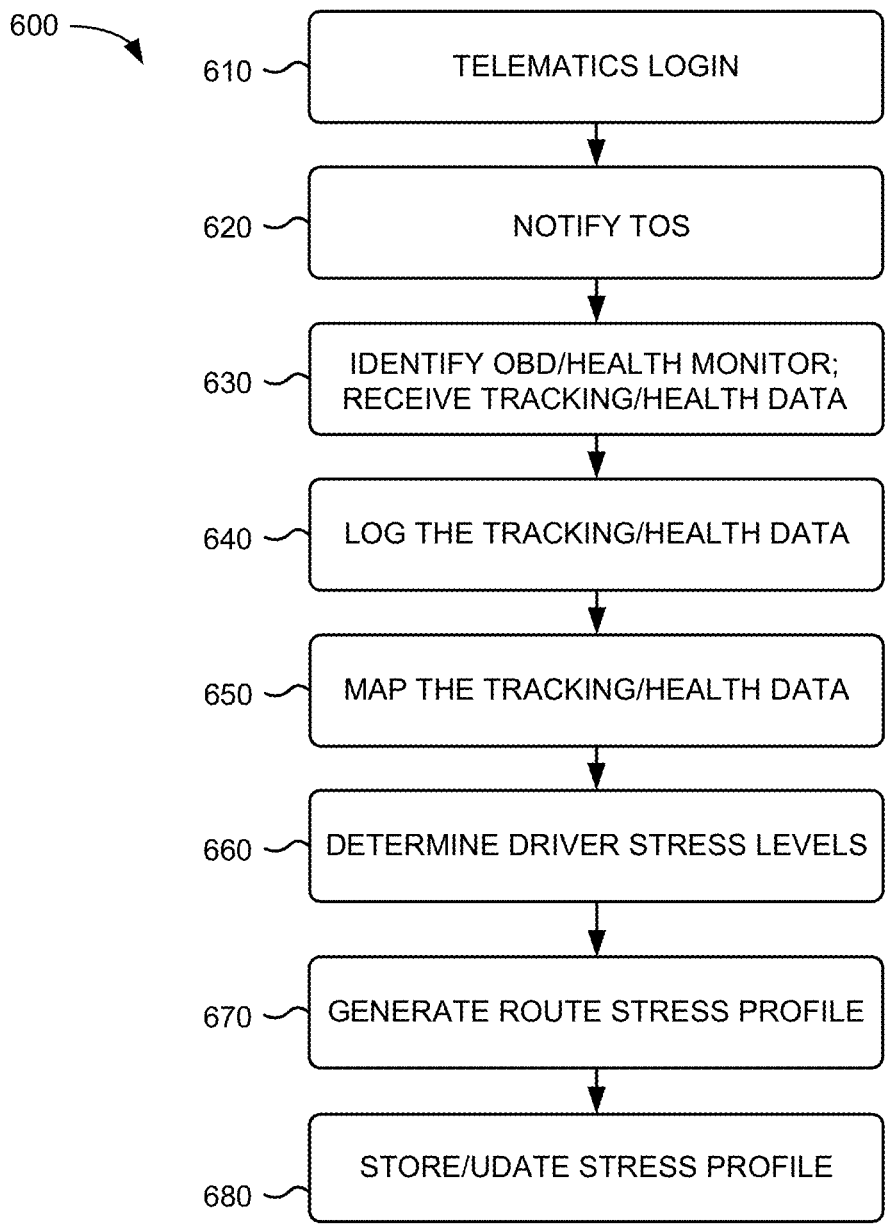
FIGS. 6 and 9 are flowcharts of processes for customized route navigation via the according to an implementation described herein.

FIG. 6 is a flowchart of an exemplary process 600 for performing contextual route navigation with respect to an operator of vehicle 110 according to an implementation described herein. In some implementations, operations depicted in FIG. 6 may be performed by vehicle computer device 115, OBD interface 120, Bluetooth®-enabled device 125, user device 130, and/or health monitor 140 individually or in combination. In other implementations, some aspects of process 600 may be performed by another device or a group of devices separate from the exemplary devices. For example, some or all of the blocks of process 600 may be performed by TOS 160.

Process 600 may begin with user device 130, associated with a subscriber to a telematics service, being used by the subscriber to log into the telematics service (block 610). For example, the subscriber may use an application ("app") that is resident on user device 130 to enter user identification (ID), for example, which was used to register the subscriber. Upon entry of the userID, the mobile app on user device 130 may transmit an activation message over a connection established via network 150 to TOS 160, and/or via a short-range wireless connection to health monitor 140 (block 620).

Activator 410 may determine that the subscriber is registered with the telematics service and may identify OBD interface 120 and health monitor 140 as being associated with the subscriber, for example, using an identifier associated with the subscriber, the mobile app, and/or user device 130. TOS 160 establishes a connection to OBD interface 120 via network 150 to begin receiving tracking data for vehicle 110, and to health monitor 140 via network 150 to begin receiving health data for the subscriber (block 630).

Figure 7:
FIG. 7 is an exemplary telematics trip data log according to an implementation described herein.

Data collector 420 may receive the tracking data via vehicle interface 450 and the health data via health monitor interface 440 and log the information, for example, as shown in the screenshot 700 illustrated in FIG. 7 (block 640). The tracking data and the physiological data may be updated at regular and/or irregular intervals (e.g., 1 sec., 2 secs., 3 secs, etc.) and stored in any suitable format, and may be made accessible for viewing. The tracking data and the health data may cease being obtained when the trip is completed and/or when operator stops the app.

Process 600 may include correlation unit 460 using the data retrieved from data collector 420 to map the tracking data to the health data for the completed trip (block 650). For example, the subscriber's heart rate may be plotted at points along a tracked travel route, as illustrated in the user interface screenshot 800 shown in FIG. 8. User interface screenshot 800 may be presented, via user device interface 430, to the subscriber via user device 130.

Process 600 may include converter 470 using the tracking data and the corresponding health data to assess the subscriber's stress along the route driven (block 660). For example, converter 470 may identify changes in the subscriber's heart rate at different locations along the travel route, and determine points at which the heart rate is elevated relative to other points along the travel route. In some embodiments, converter 470 may retrieve baseline heart rate information from medical history information that is stored in DB 425. For example, medical records may be obtained from a medical provider (e.g., doctors, pharmacists, etc.) and/or health monitoring technology (e.g., sleep logs, etc.). Converter 470 may compare the obtained heart rate information to the baseline values in assessing the associated stress. In other embodiments, the baseline values may be determined using physiological data from multiple other drivers.

Figure 8:
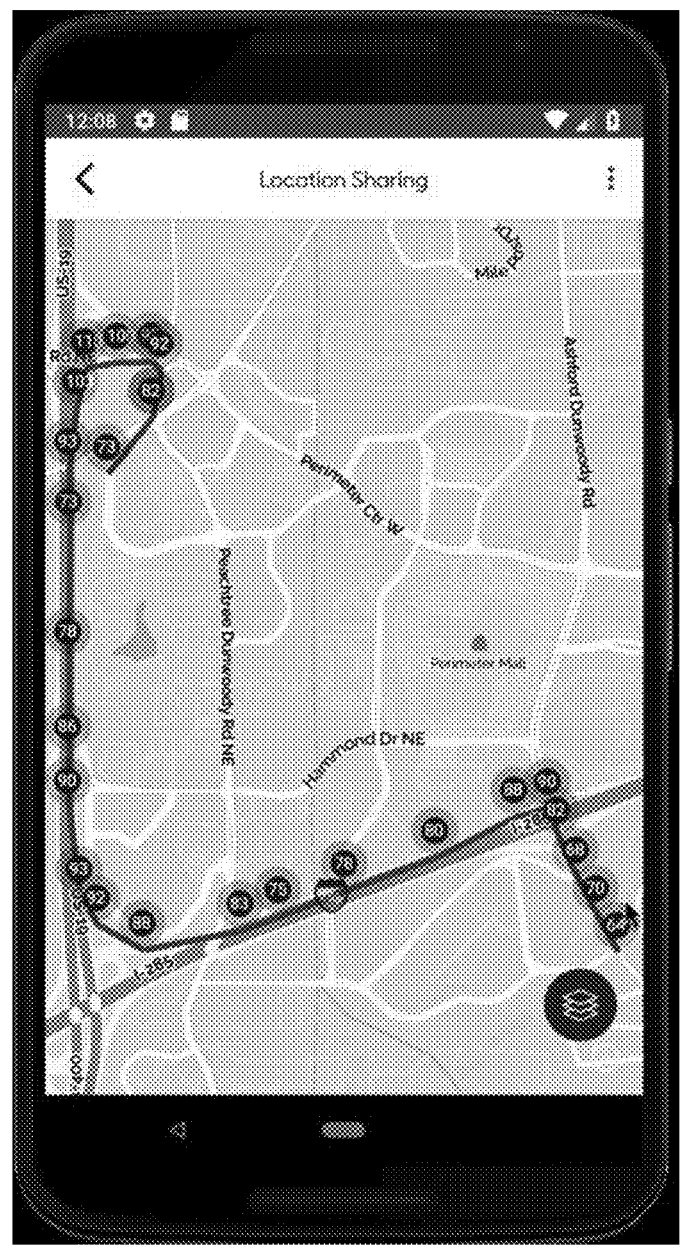
FIGS. 8 and 10 are exemplary user interfaces related to route navigation according to an implementation described herein.

Using the assessed stress indicators, converter 470 may generate a stress profile for the subscriber for individual segments of the route and/or for the overall route (block 670). Referring to FIG. 8, the route segment that includes triple-digit values (i.e., 103, 110, and 100) may be classified as high stress. Threshold values may be used to determine varied stress classifications. Threshold values may be predetermined based on physiological data obtained from multiple other drivers.

DB 425 may store the stress profile and update it at any time that subscriber re-travels any portion of the route and the telematics service is activated (block 680). In updating the stress profile, converter 470 may average multiple stress profile scores. Additionally or alternatively, converter 470 may distinguish the stress profiles based on some other criteria associated with the different stress profiles. For example, the stress profiles may have been generated for travel at different times of the day (e.g., rush hour and non-rush hour) or days of the week (e.g., weekday and/or weekend). In some embodiments, for future use in navigation recommendation decisions, the stress profile corresponding to the time-of-day and/or day-of-the-week may be the stress profile that is used for determining the route recommendation.

Figure 9:
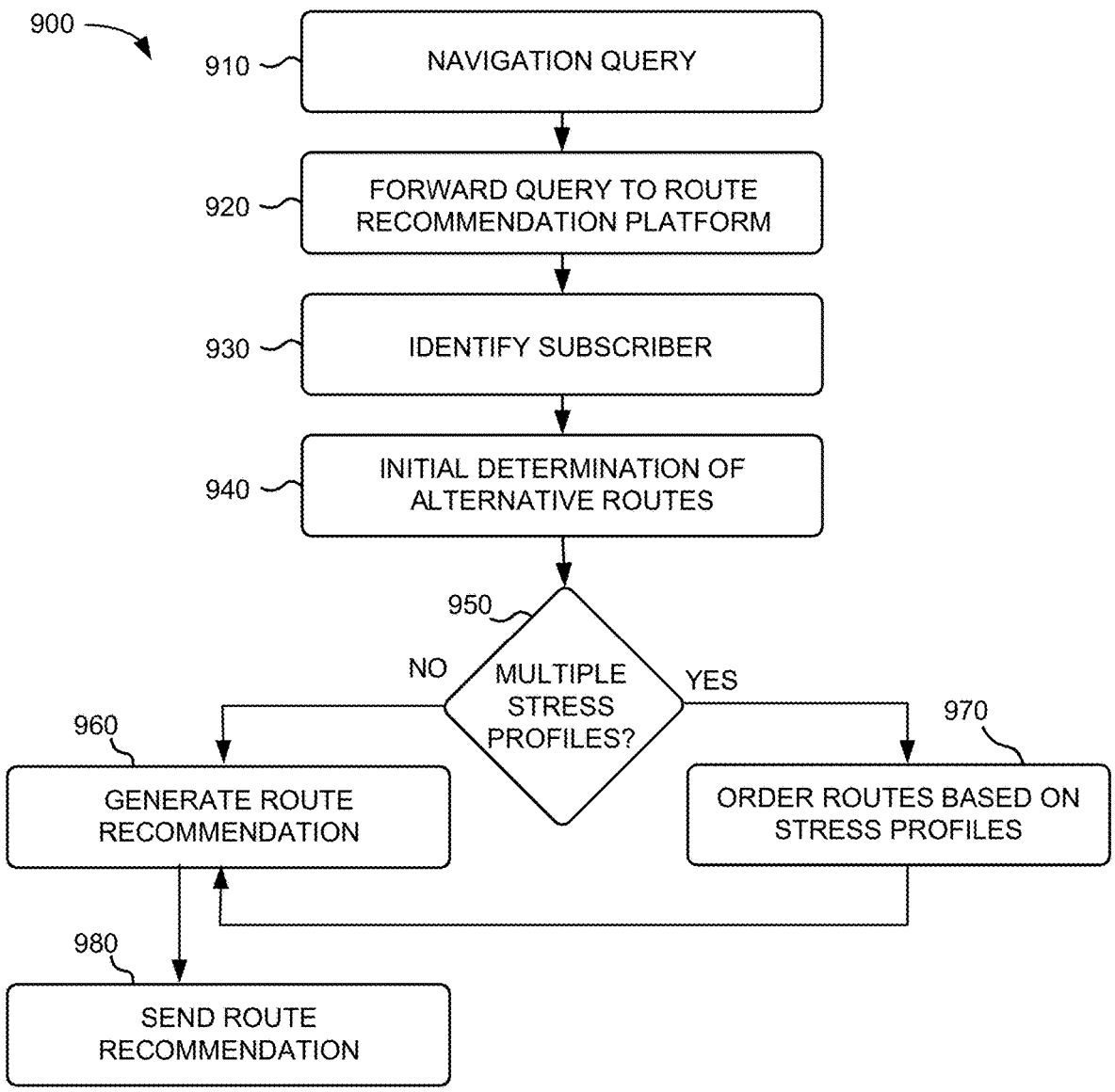

FIG. 9 is an exemplary process 900 for automatically providing customized route recommendation responsive to a navigation query received from an operator of vehicle 110, according to an implementation described herein. In some implementations, operations depicted in FIG. 9 may be performed by vehicle computer device 115, OBD interface 120, speaker device 125, user device 130, and/or health monitor 140 individually or in combination. In other implementations, some aspects of process 900 may be performed by another device or a group of devices separate from the exemplary devices. For example, some or all of the blocks of process 900 may be performed by TOS 160.

Process 900 may begin with user device 130, associated with a subscriber to a telematics service, being used by the subscriber to submit a navigation query (block 910). For example, the subscriber may use navigation that is resident on user device 130 to enter a destination. In some embodiments, the point of origination may be the current location of user device. The mobile app on user device 130 may forward the navigation query over a connection established via network 150 to route recommendation platform 400 (block 920).

Route recommendation platform 400 may determine that the subscriber is registered with the telematics service (block 930). Route recommendation platform 400 may perform initial route determination based on the identified destination and criteria such as travel time and distance to identify alternative travel routes (block 940). Route recommendation platform 400 may determine whether more than one of the alternative travel routes have a stress profile associated with one more segment of the travel routes (block 950).

If route recommendation platform 400 determines that none or only one of the alternative routes has an associated stress profile (block 950—NO), route recommendation platform 400 generates a route recommendation presenting one or more of the alternative travel routes. If route recommendation platform 400 determines that more than one of the alternative routes has an associated stress profile (block 950—YES), route recommendation platform 400 rank orders the alternative travel routes based on the associated stress profiles (block 970). In some embodiments, when no or insufficient tracking and health data for the particular subscriber are available to generate a stress profile for a particular route/segment, route recommendation platform 400 may use stress profiles generated using data obtained from other users to rank order the recommended travel routes.

Figure 10:
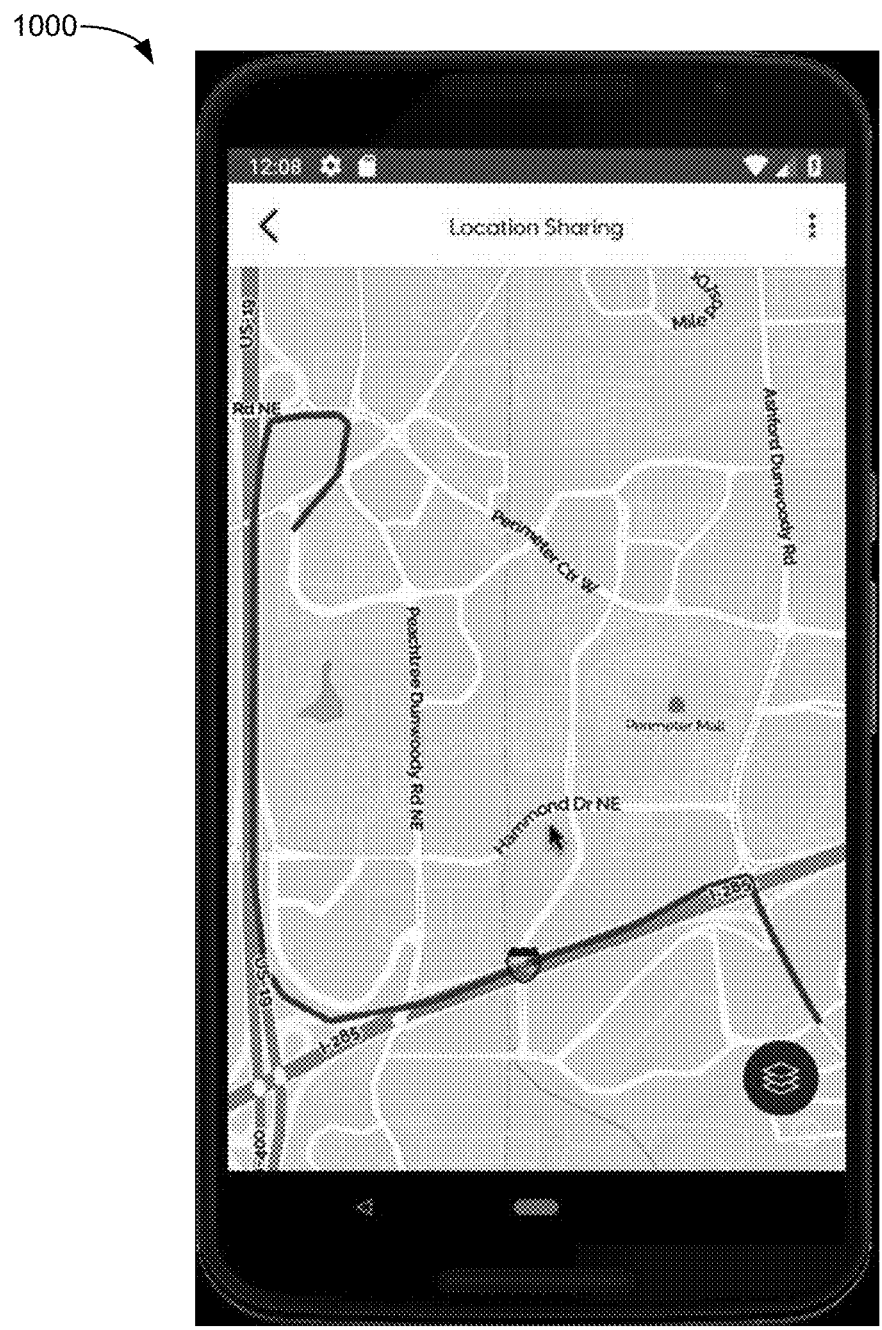

Based on the ranked order, route recommendation platform 400 may generate a route recommendation including one or more of that recommended routes (block 960). Route recommendation platform 400 may transmit via network 150 the route recommendation to user device 130 (block 980) for presentation via a user interface 1000 (FIG. 10).

In addition to using health data to determine driver "stress," other states of health may be determined depending on the health data obtained. For example, eye movement and other indicators may be used to assess driver fatigue. In one embodiment, the above-described systems may retrieve sleep logs for the operator for use in determining a state of driver fatigue and/or level of alertness. Sleep logs may be generated by health monitors worn by the driver. Eye-movement data may also be used in determining driver fatigue and/or alertness.

In addition to using "health data" to assess driver stress and other health states, the systems described above may use other criteria that is obtained for the driver. In one embodiment, for example, the steering wheel may include dynamometric sensors that measure the driver's grip on the steering wheel. Hand tension may be an indicator of the driver's stress level. In another embodiment, the driver's use of the car's horn may be detected, and the frequency of horn use may be used to determine driver stress levels. In yet another embodiment, the microphone in Bluetooth®-enabled device 125 may record voice input from the driver. The systems described above may analyze the driver's voice input to determine, for example, whether the driver yells, mutter, and/or uses expletives. The systems may use this analysis in determining the driver's stress level. Other indicators may be used.

In other embodiments, the telematics data may be used to determine that an operator/vehicle have been involved in an accident. The telematics service may automatically notify emergency responders. In notifying the emergency responders, the telematics service may automatically provide the emergency responders with some or all of the available physiological data for the operator.

In some embodiments, when a determination is made that insufficient health information and tracking data are available for an operator to perform personalized route recommendation, the system described herein may use health information and tracking data from other operators over a particular timeframe.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

As an example, while series of blocks have been described with respect to FIG. 6 and FIG. 9, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or an FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

To the extent the aforementioned embodiments collect, store or employ personal information of individuals, it should be understood that such information shall be used in accordance with all applicable laws concerning protection of personal information. Additionally, the collection, storage, and use of such information may be subject to consent of the individual to such activity, for example, through well known "opt-in" or "opt-out" processes as may be appropriate for the situation and type of information. Storage and use of personal information may be in an appropriately secure manner reflective of the type of information, for example, through various encryption and anonymization techniques for particularly sensitive information.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A system comprising:

an on-board diagnostic (OBD) interface to couple to a diagnostic port of a motor vehicle and transmit, via a wireless network, telematics data collected during an operation of the motor vehicle;

a monitoring device to obtain physiological data for an operator of the motor vehicle at corresponding points in time during the operation of the motor vehicle, and transmit the physiological data via the wireless network; and a network device configured to:

receive, via the wireless network, the telematics data to determine multiple roadway locations of the motor vehicle at the corresponding points in time, receive, via the wireless network, the physiological data to determine a physiological state of the operator at each of the multiple roadway locations at the corresponding points in time, determine, using the physiological states, a stress level profile associated with the operator for multiple segments of each travel route of a plurality of travel routes to a destination and including one or more of the multiple roadway locations, determine that, for at least one segment of at least one of the plurality of travel routes, an amount of the operator's physiological data is insufficient for determining the stress level profile, obtain, based on the determination that the amount of the operator's physiological data is insufficient, a stored stress level profile associated with another operator for the at least one segment, assign, using the stored stress level profile associated with the other operator and the stress level profiles associated with the operator, a relative stress level profile value to each travel route, rank order a set of the travel routes according to the relative stress level profile values, and send, to the operator via the wireless network, a recommendation identifying the set of the travel routes in the rank order.

2. The system of claim 1, wherein the telematics data includes at least one of braking information, acceleration information, geographic information, speed of the motor vehicle, time-of-day information, or vehicle performance data.

3. The system of claim 1, wherein the physiological data includes at least one of a heart rate, blood pressure, blood sugar levels, body temperature, perspiration, respiratory rate, hormone levels, eye movement, or dynamometric values.

4. The system of claim 1, wherein the network device is further configured to:
determine that the physiological state of the operator corresponds to a state of operator fatigue at a particular roadway location, and
send, responsive to the state of operator fatigue, an alert to the operator via the OBD interface, the monitoring device, and a user device associated with the operator.

5. The system of claim 1, wherein the network device is further configured to:
recommend, to another operator of another motor vehicle, the set of travel routes responsive to a navigation query received from the other operator.

6. The system of claim 1, wherein the network device is further configured to:
receive, from the monitoring device, other physiological data obtained for the operator when the operator is not operating any motor vehicle,
determine, using the other physiological data, a baseline physiological state for the operator, and
determine the physiological state of the operator using the baseline physiological state.

7. The system of claim 1, wherein the network device is further configured to:
compare the physiological data to stored physiological data for the operator contained in a stored medical history, wherein the network device determines the physiological state of the operator based on results of the comparison.

8. A method comprising:
transmitting, via a wireless network from an on-board diagnostic (OBD) interface coupled to a diagnostic port of a motor vehicle, telematics data collected during an operation of the motor vehicle;

transmitting, via the wireless network from a monitoring device, physiological data obtained for an operator of the motor vehicle at corresponding points in time during the operation of the motor vehicle;

determining, by a network device, multiple roadway locations of the motor vehicle at the corresponding points in time, using the telematics data received via the wireless network;

determining, by the network device, a physiological state of the operator at each of the multiple roadway locations at the corresponding points in time, using the physiological data received via the wireless network;

determining, by the network device using the physiological states, a stress level profile associated with the operator for multiple segments of each travel route of a plurality of travel routes to a destination and including one or more of the multiple roadway locations;

determining that, for at least one segment of at least one of the plurality of travel routes, an amount of the operator's physiological data is insufficient for determining the stress level profile, obtaining, based on the determination that the amount of the operator's physiological data is insufficient, a stored stress level profile associated with another operator for the at least one segment, assigning, using the stored stress level profile associated with the other operator and the stress level profiles associated with the operator, a relative stress level profile value to each travel route;

rank ordering a set of the travel routes according to the relative stress level profile values; and sending, by the network device to the operator via the wireless network, a recommendation identifying the set of the travel routes in the rank order.

9. The method of claim 8, wherein the telematics data includes at least one of braking information, acceleration information, geographic information, speed of the motor vehicle, time-of-day information, or vehicle performance data.

10. The method of claim 8, wherein the physiological data includes a heart rate, blood pressure, blood sugar levels, body temperature, perspiration, respiratory rate, hormone levels, eye movement, and dynamometric values.

11. The method of claim 8, further comprising:
determining that the physiological state of the operator corresponds to a state of operator fatigue at a particular roadway location; and
sending, responsive to the state of operator fatigue, an alert to the operator via at least one of the OBD interface, the monitoring device, or a user device associated with the operator.

12. The method of claim 8, further comprising:
recommending, to another operator of another motor vehicle, the set of travel routes responsive to a navigation query received from the other operator.

13. The method of claim 8, further comprising:
receiving, from the monitoring device, other physiological data obtained for the operator when the operator is not operating any motor vehicle,
determining, using the other physiological data, a baseline physiological state for the operator, and
determining the physiological state of the operator using the baseline physiological state.

14. The method of claim 8, further comprising:
comparing the physiological data to stored physiological data for the operator contained in a stored medical history; and
determining the physiological state of the operator based on results of the comparison.

15. A non-transitory, computer-readable storage medium storing instructions executable by a processor of a computational device, which when executed cause the computational device to:
transmit, via a wireless network from an on-board diagnostic (OBD) interface coupled to a diagnostic port of a motor vehicle, telematics data collected during an operation of the motor vehicle;
transmit, via the wireless network from a monitoring device, physiological data obtained for an operator of the motor vehicle at corresponding points in time during the operation of the motor vehicle;
determine multiple roadway locations of the motor vehicle at the corresponding points in time, using the telematics data received via the wireless network;
determine a physiological state of the operator at each of the multiple roadway locations at the corresponding points in time, using the physiological data received via the wireless network;
determine, using the physiological states, a stress level profile associated with the operator for multiple segments of each travel route of a plurality of travel routes to a destination and including one or more of the multiple roadway locations;
determine that, for at least one segment of at least one of the plurality of travel routes, an amount of the operator's physiological data is insufficient for determining the stress level profile,
obtain, based on the determination that the amount of the operator's physiological data is insufficient, a stored stress level profile associated with another operator for the at least one segment,
assign, using the stored stress level profile associated with the other operator and the stress level profiles associated with the operator, a relative stress level profile value to each travel route;
rank order a set of the travel routes according to the relative stress level profile values; and
send, to the operator via the wireless network, a recommendation identifying the set of the travel routes in the rank order.

16. The non-transitory, computer-readable storage medium of claim 15, wherein the telematics data includes braking information, acceleration information, geographic information, speed, time-of-day information, and vehicle performance data.

17. The non-transitory, computer-readable storage medium of claim 15, wherein the physiological data includes at least one of a heart rate, blood pressure, blood sugar levels, body temperature, perspiration, respiratory rate, hormone levels, eye movement, or dynamometric values.

18. The non-transitory, computer-readable storage medium of claim 15, wherein executing the instructions further cause the computational device to:
determine that the physiological state of the operator corresponds to a state of operator fatigue at a particular roadway location; and
send, responsive to the state of operator fatigue, an alert to the operator via at least one of the OBD interface, the monitoring device, or a user device associated with the operator.

19. The non-transitory, computer-readable storage medium of claim 15, wherein executing the instructions further cause the computational device to:
receive, from the monitoring device, other physiological data obtained for the operator when the operator is not operating any motor vehicle,
determine, using the other physiological data, a baseline physiological state for the operator, and
determine the physiological state of the operator using the baseline physiological state.

20. The non-transitory, computer-readable storage medium of claim 15, wherein executing the instructions further cause the computational device to:
compare the physiological data to stored physiological data for the operator contained in a stored medical history; and
determine the physiological state of the operator based on results of the comparison.

* * * * *